United States Patent [19]
Riggs

[11] Patent Number: 5,814,276
[45] Date of Patent: Sep. 29, 1998

[54] AUTOMATED BLOOD SAMPLE PROCESSING SYSTEM

[76] Inventor: Robert C. Riggs, 12901 N. MacArthur, #102, Oklahoma City, Okla. 73142

[21] Appl. No.: 637,541

[22] Filed: Apr. 25, 1996

[51] Int. Cl.[6] .................................................. G01N 35/02
[52] U.S. Cl. ................ 422/65; 422/63; 422/67; 422/72; 422/100; 436/43; 436/45; 436/47; 436/49; 436/50; 436/180
[58] Field of Search ............................ 422/63, 65, 100, 422/101, 72, 104, 67; 436/43, 45, 47, 48, 49, 50, 174, 180

[56] References Cited

U.S. PATENT DOCUMENTS

| | | | |
|---|---|---|---|
| 3,151,073 | 9/1964 | Anthon | 233/4 |
| 3,544,272 | 12/1970 | Vails | 422/65 |
| 3,826,622 | 7/1974 | Natelson | 23/259 |
| 3,883,305 | 5/1975 | Hoskins et al. | 23/253 |
| 3,944,133 | 3/1976 | Kessell et al. | 233/26 |
| 4,595,563 | 6/1986 | Degrave | 422/72 |
| 4,740,472 | 4/1988 | Burtis et al. | 436/63 |
| 4,855,909 | 8/1989 | Vincent et al. | 364/413.01 |
| 4,906,432 | 3/1990 | Geiselman | 422/63 |
| 4,927,545 | 5/1990 | Roginski | 210/745 |
| 4,933,291 | 6/1990 | Daiss et al. | 436/45 |
| 4,982,553 | 1/1991 | Itoh | 53/246 |
| 5,071,625 | 12/1991 | Kelln et al. | 422/72 |
| 5,122,343 | 6/1992 | Ishizaka et al. | 422/66 |
| 5,128,105 | 7/1992 | Berhold et al. | 422/104 |
| 5,207,986 | 5/1993 | Kadota et al. | 422/65 |
| 5,350,564 | 9/1994 | Mazza et al. | 422/63 |
| 5,356,595 | 10/1994 | Kanamori et al. | 422/65 |
| 5,362,648 | 11/1994 | Koreyasu et al. | 436/48 |
| 5,380,488 | 1/1995 | Wakatake | 422/65 |
| 5,389,339 | 2/1995 | Petschek et al. | 422/64 |
| 5,409,665 | 4/1995 | Burd | 422/64 |
| 5,460,057 | 10/1995 | Ostrup | 73/864.81 |
| 5,472,669 | 12/1995 | Miki et al. | 422/63 |

*Primary Examiner*—Long V. Le
*Attorney, Agent, or Firm*—Head, Johnson & Kachigian

[57] ABSTRACT

An automated blood sample processing system having a primary test tube loader in which primary test tubes having blood samples are placed, a conveyor system for moving test tubes in selectable routes, a centrifuge, a secondary test tube loading area in which empty secondary test tubes are loaded for transportation by the conveyor system, a pipetting system into which primary test tubes and empty secondary test tubes are moved by the conveyor system, the pipetting system serving to aliquot centrifuged samples from each of the primary test tubes into a selected number of secondary test tubes, a bar code printer for printing and attaching a bar code label to each of the secondary test tubes, a capper system into which the secondary test tubes are moved by the conveyor system for attaching a cap to each of the secondary test tubes and a sortation system in which the secondary test tubes are moved by the conveyor system and in which the secondary test tubes are sorted into separate slots in a sortation tray, the secondary test tubes being available for removal from the sortation tray slots for subsequent processing. The system may also include a printer for requisitions disclosing patient demographic and requisition information for use in dispatching batches of labeled secondary tubes.

14 Claims, 2 Drawing Sheets

5,814,276

AUTOMATED BLOOD SAMPLE PROCESSING SYSTEM

REFERENCE TO PENDING APPLICATIONS

This application is not related to any pending United States or foreign patent applications.

REFERENCE TO MICROFICHE APPENDIX

This application is not referenced in any microfiche appendix.

BACKGROUND OF THE INVENTION

1. Field of the Invention

This invention relates to an automated blood sample processing system for processing primary test tubes each having a blood sample therein in a system wherein the test tubes are passed through a centrifuge to separate serum from other blood components and thereafter the blood samples are passed to a pipetting system into which primary samples are aliquoted into secondary test tubes and identified with a bar code label.

2. Description of Related Art

Modern day blood analysis procedures require that primary blood samples, as drawn from patients, be subjected to a sequence of steps which, if practiced entirely manually, are exceedingly time consuming. Due to the increasingly large number of blood analysises performed as a part of societies' continuing effort to improve and economize health care services, need exists for streamlining the process. For this reason, others have provided systems for automating certain blood sampling procedures. As an example, U.S. Pat. No. 4,927,545 entitled "Method and Apparatus For Automated Processing and Analysis of Blood Serum" provides a method of centrifugation of test tubes containing blood specimens including the use of a robotic arm for moving test tubes into and out of a centrifuge. The teachings of U.S. Pat. No. 4,927,545 are herein adopted by reference in this present application.

U.S. Pat. No. 4,595,563 entitled "Apparatus For Sample Transfer and Analysis For Centrifugation" teaches another system wherein centrifugation of blood samples can be carried out by automated means.

Still another example of the automation of the processing of blood samples, and particularly for the centrifugation thereof, U.S. Pat. No. 3,826,622 entitled "Containers For Use In An Automated Centrifuge" discloses specially shaped containers for use in an automated system.

U.S. Pat. No. 3,944,133 entitled "Automated Centrifuge" illustrates and describes another automated arrangement for subjecting blood specimens to centrifugal force to separate the serum and other components for further processing.

For additional background information relating to the automated processing of blood samples, reference may also be had to United States patents:

| Pat. No. | INVENTOR | TITLE |
| --- | --- | --- |
| 3,151,073 | Anthon | Centrifuging Apparatus |
| 3,883,305 | Hoskins et al. | Automatic Chemical Analysis Apparatus |
| 4,906,432 | Geiselman | Liquid Handling |
| 4,933,291 | Daiss et al. | Centrifugable Pipette Tip And Pipette Therefor |

-continued

| Pat. No. | INVENTOR | TITLE |
| --- | --- | --- |
| 5,071,625 | Kelin et al. | Cuvette Handling |
| 5,389,339 | Petschek et al. | Integral Biomolecule Preparation Device |
| 5,409,665 | Burd | Simultaneous Cuvette Filling With Means To Isolate Cuvettes |

While each of the above-mentioned United States patents show systems for improving the efficiency of handling blood samples, and particularly for improving the efficiency of subjecting blood samples to centrifugation, none of these references show a complete system for handling blood samples that substantially speeds up the preparation of blood specimens for laboratory analysis.

BRIEF SUMMARY OF THE INVENTION

An automated blood sample processing system is provided in which primary test tubes each having a blood sample drawn from a patient are loaded. A conveyor system moves the test tubes along selectable routes.

A centrifuge is employed for separating blood serum from other blood components. After centrifugation the conveyor system moves the primary test tubes to a pipetting system.

A secondary test tube loading area receives empty secondary test tubes that are conveyed to the pipetting system.

In the pipetting system into which primary and empty secondary test tubes are moved by the conveyor system, means is provided to aliquot serum samples from each of the primary test tubes into selected numbers of secondary test tubes.

The number of aliquots performed by the pipetting system for each blood sample is controlled by a system computer that responds to a comparison of patient data input with a bar code label provided on each of the primary test tubes.

After being supplied with serum samples, a bar code label is applied to each of the secondary test tubes employing information supplied by the system computer.

The secondary test tubes are then moved by the conveyor system to a capper system wherein caps or stoppers are affixed. After capping, the secondary test tubes are moved by the conveyor system to a sortation system in which each are sorted into separate slots in a sortation tray where they may be removed for subsequent processing.

The conveyor system includes accumulation areas at various stages, such as in advance of the centrifuge where test tubes are arrayed in queues while awaiting processing. An accumulation area is also provided in advance of the pipetting system where both primary and secondary test tubes are held in reserve.

The system computer may be connected to a remotely located host computer wherein patient information is stored. Information available from the host computer controls the number of aliquots of each blood sample performed in the pipetting system and for the input of information into the bar code printer to insure that proper information is applied to each of the secondary test tubes.

A more complete understanding of the invention will be obtained from the following detailed description of the preferred embodiment and the claims, taken in conjunction with the attached drawings.

DETAILED DESCRIPTION OF THE PREFERRED EMBODIMENTS

The automated blood sample processing system of this invention comprises five basic subsystems as follows:

1) a conveyor system for moving test tubes in selected routes;
2) a centrifugation system;
3) a pipetting system;
4) a bar code printer and attachment system; and
5) a sortation system.

Figure 1:
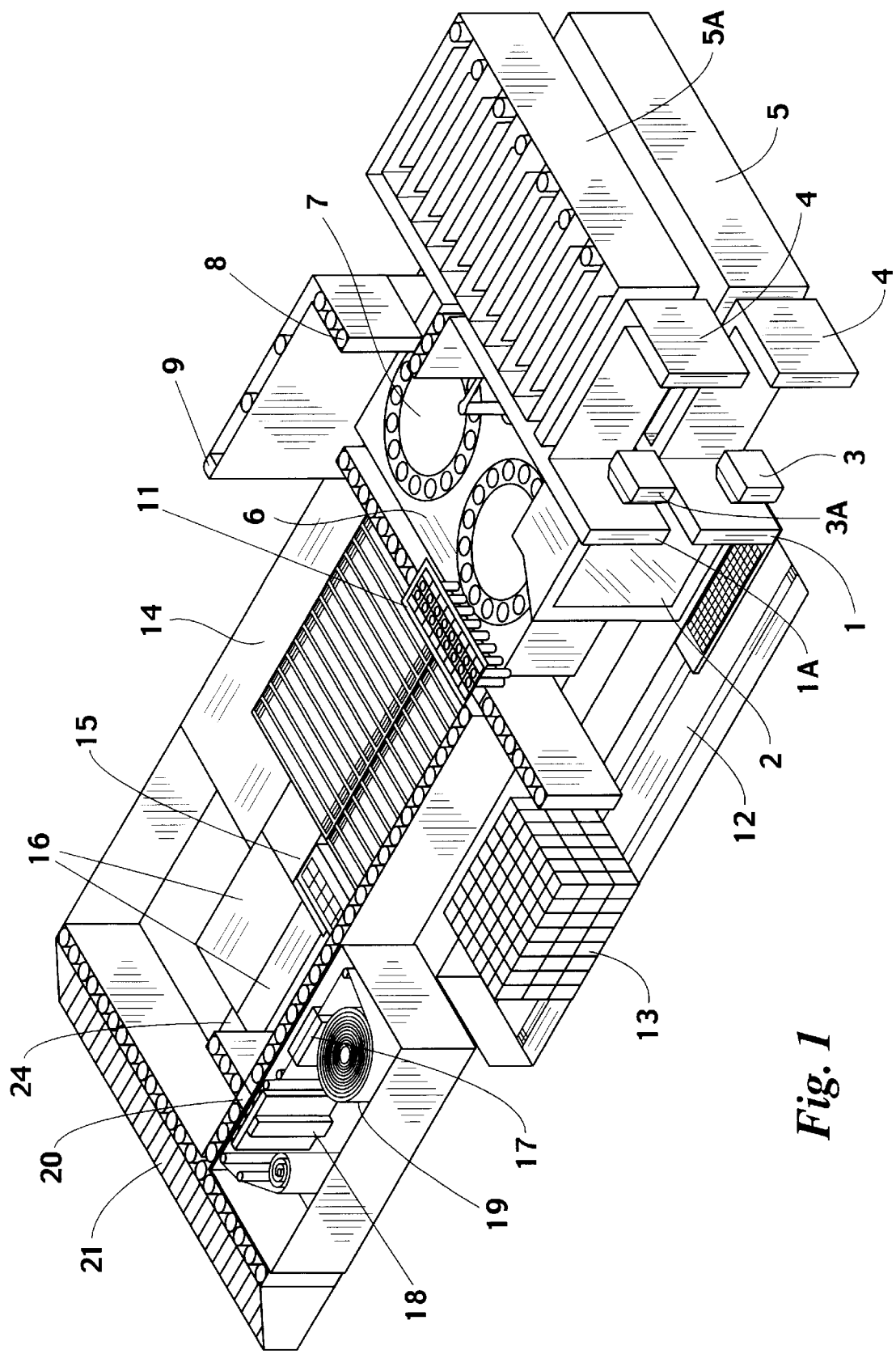
FIG. 1 is an isometric illustration of an automated blood sample processing system incorporating the principles of the invention.

The basic elements making up these subsystems will be described by reference to FIGS. 1 and 2. FIG. 1 shows an isometric arrangement of the system, while FIG. 2 shows a plan view.

Figure 2:
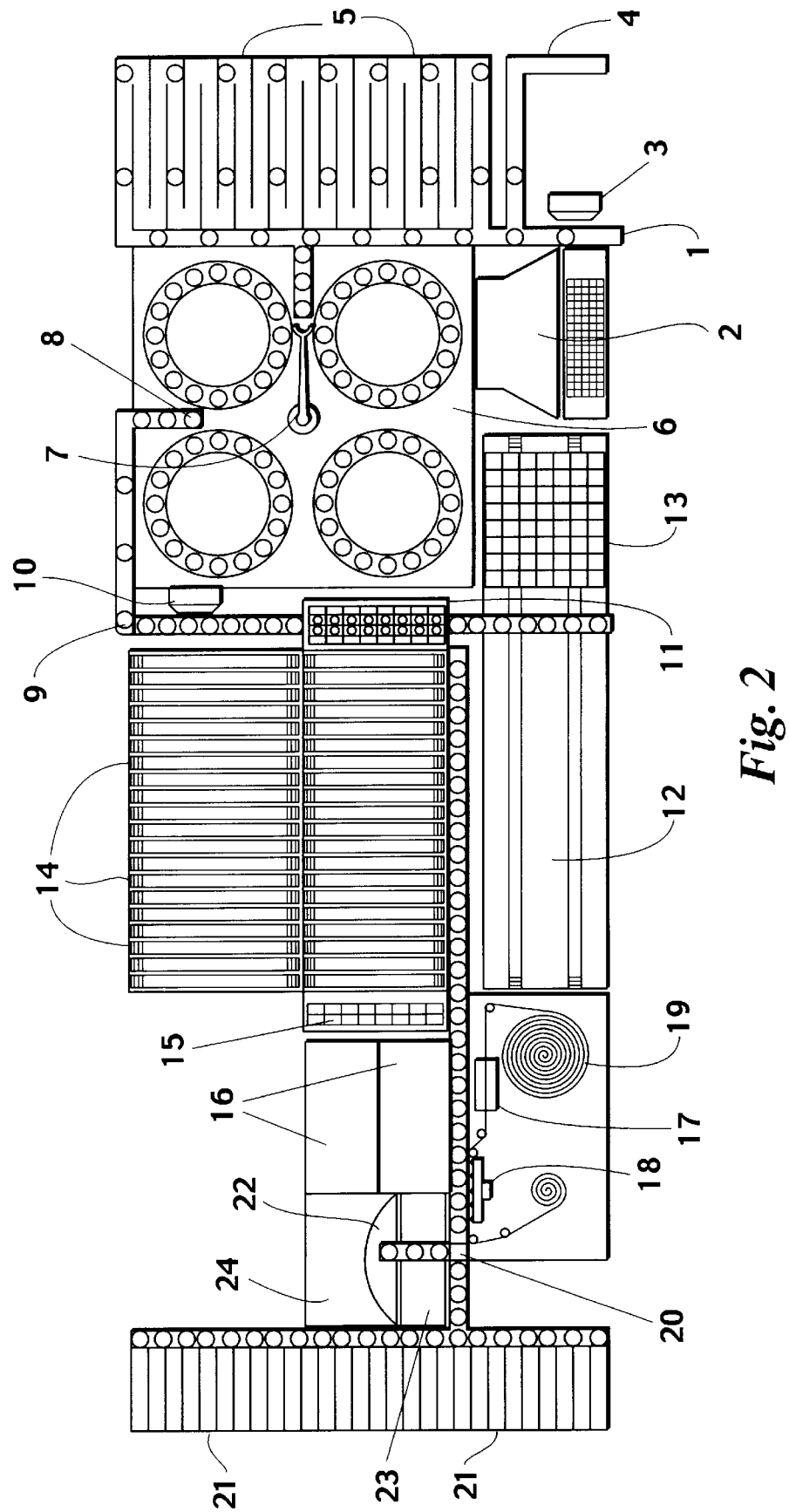
FIG. 2 is a plan view of the system of FIG. 1. In both FIGS. 1 and 2 the various stages of the system are illustrated diagrammatically.

FIGS. 1 and 2 illustrate the sequential relationship of the subsystems and subcomponents in a diagrammatic fashion. The subsystems are not illustrated in detail since they are separately commercially available, or are within the skills of practitioners in the relevant art. The system provides an automated, efficient and economical means of moving individual blood samples, each contained in a test tube as drawn from a patient through the steps necessary to provide a plurality of aliquoted serum specimens in separate secondary test tubes, each properly labeled by a bar code label that identifies the patient from which the specimen has been drawn.

Primary test tubes, each having a sufficient blood specimen and each provided with a bar code label, are placed into a first primary test tube load area 1. The specimen contained in each test tube located in first primary test tube load area 1A is as drawn from a patient, that is, before centrifugation or other effort to separate the blood specimen into serum and other blood components. Specimens that have been centrifuged are manually placed into a second primary test tube load area 1. The test tubes placed in second test tube load area 1 may be said to have been "spun" and therefore do not require further centrifugation.

Before placement of test tubes into the system, either in the first primary test tube load area 1A or the second primary test tube load area 1, bar code labels may be applied. These bar code labels provide information as to the patient and as a minimum, identify the patient's record or accession number. If a test tube containing a blood specimen drawn from a patient is not provided with a bar code label, the information concerning the patient is input into system computer 2 so that the position assigned to each of the primary test tubes in the conveyor transportation system can be established.

System computer 2, which may be also termed a "central processing unit terminal", may be interconnected with a host computer (not seen), in which case the host computer will have the patient information in its data bank that will be accessible by system computer 2. The host computer can, for example, be a central processing unit for a laboratory wherein the system of FIGS. 1 and 2 is employed. System computer 2, when connected with a host computer, will access the host computer for each patient through a host query. System computer 2 will then assign the number of aliquots needed within the pipetting system, all to be described subsequently.

Primary test tubes inserted into the system, whether in first primary test tube loading area 1A for unspun test tubes or second primary test tube loading area 1 for test tubes holding samples which have already been centrifuged, will be routed past a bar code scanner. Test tubes loaded in first primary tube loading area 1A will pass bar code scanner 3A, while test tubes loaded into second primary test tube loading area 1 will pass bar code scanner 3. Information gathered by bar code scanners 3 and 3A is fed to system computer 2, which information will call up instructions from system computer 2 or additionally from a host computer (if a host computer is employed) and which information will be employed in the system. A test tube that passes bar code scanners 3 or 3A having bar coded information that is unreadable, missing or does not conform to the data bank information within system computer 2 or a host computer, will be diverted by the conveyor system to reject conveyor 4 where rejected test tubes are accumulated to be physically removed.

All test tubes that pass bar code scanner 3 or 3A and are not rejected are conveyed by the conveyor system to an accumulation area 5 or 5A where the test tubes will be arrayed in queues for passage. Test tubes passing from second primary tube load area 1 that have been spun and that are approved for further processing by system computer 2 are conveyed to accumulation area 5. Thus, accumulation area 5A stores test tubes that need to be centrifuged, while accumulation area 5 stores test tubes that have already been centrifuged.

A centrifuge system is indicated by the numeral 6. The function of the centrifuge system is to subject the blood samples contained within the test tubes to centrifugal force by spinning to separate blood serum from other blood components. The test tubes contained within accumulation area 5, which have been spun in a centrifuge, do not need to pass through centrifuge area 6, however, those contained within accumulation area 5A must be centrifuged before further processing. These "unspun" test tubes are loaded into a centrifuge within centrifuge areas 6 by means of a robotic arm 7. An example of a robotic arm for moving test tubes from one location to another is illustrated in U.S. Pat. No. 4,927,545. The test tubes from accumulation area 5A are loaded individually into a centrifuge until a centrifuge is full. To speed up the process, a plurality of different centrifuges may be employed (4 being shown in FIGS. 1 and 2), however, the total number may vary from one to many. After a centrifuge is fully loaded, it rotates to spin the test tubes at a sufficient rate to generate a preselected amount of centrifugal force for a preselected time, all well known to manufacturers of centrifuges as employed in the processing of blood specimens.

After a centrifuge has operated for an established length of time, the test tubes therein will be removed by robotic arm 7 and loaded into conveyor track 8 that is a portion of the conveyor system.

From conveyor track 8, the test tubes, after having been centrifuged or "spun", are moved by the conveyor system to a tube elevator drop 9 where they are merged with the spun tubes originally stored in accumulation area 5 that have bypassed centrifuge area 6. At this point, all of the test tubes moving in the conveyor system have been centrifuged and all pass a second bar code scanner 10 (see FIG. 2). The output of bar code scanner 10 is supplied to system computer 2 which, in turn, provides instructions from a program stored within the computer to operate a pipetting system and assign subsequent bar code labels to the secondary test tubes.

All of the primary test tubes moving in the conveyor system past second bar code scanner 10 have been centrifuged, and the blood samples contained therein are ready to be aliquoted in the pipetting system. For this purpose, the test tubes are aligned under a multi-tip pipetting arm 11 which, upon instructions from system computer 2, will draw appropriate amounts of serum or plasma from each of the primary test tubes, the amount of serum or plasma being withdrawn depending upon testing levels determined by a computer program stored in system computer 2.

After serum or plasma has been aspirated from a sequence of primary test tubes, they will be conveyed by the conveyor system to primary test tube rack area 12 and dropped into a test tube rack 13 for storage. Empty secondary test tubes will be preloaded, either manually or by some other system that is not part of this disclosure, into the secondary test tube load area 14. A primary purpose for the automated blood sample processing system of this invention is to distribute a portion of blood specimens taken from individual primary test tubes into a plurality of secondary test tubes so that they can then be passed for separate laboratory analysis. To achieve this step, the secondary test tubes are passed by the conveyor system into sequential positions under the path of multi-tip pipetting arm 11.

Pipetting arm 11 moves sequentially from a first position wherein blood specimens are aspirated from the primary test tubes into a second position in alignment with an appropriate number of secondary test tubes, wherein serum or plasma is deposited into the heretofore empty secondary test tubes. This process is continued until serum or plasma, in the required amount, is deposited in the selected number of secondary test tubes as has been instructed by the software program within system computer 2.

After all serum contained within the multi-tip pipetting arm 11 has been dispensed, it will move to wash area 15 wherein it is thoroughly cleaned. Once it has been cleaned, it moves back to the original position to pipette the next set of primary test tubes. The solution necessary to clean the multi-tip pipetting arm in wash area 15 is stored in wash containers 16.

In order to carefully control the processing of the blood plasma or serum deposited in the secondary test tubes, they are each applied with a bar code label. For this purpose, the automated blood sample processing system includes a thermal bar code printer 17 that prints individual bar code labels that are fed to a label applying mechanism 18, the stock bar code labels being contained in a spool 19. Information for operation of bar code printer 17 is, as previously indicated, supplied from system computer 2. After a label is printed in printer 17, it is affixed to the correct test tube by label applying mechanism 18.

Secondary test tubes, each containing a predetermined quantity of blood, serum or plasma and having the appropriate identifying bar code label, are then passed to a capping device 20 where a cap or stopper is placed on or in each test tube. After the test tubes have been capped at the capping device 20, they are moved by the conveyor system to a sortation tray 21 having a plurality of slots therein. Test tubes that are assigned to be sent to a reference laboratory or other location will be sorted and dropped into a send-out-bag 22 (see FIG. 2). After a send-out-bag has been filled with a predetermined number of capped secondary test tubes, a laser printer 23 will manifest a requisition containing patient demographic information obtained from the host system computer. After the capped secondary test tubes and requisition are placed into the send-out-bag 22, it will be dropped into a padded holding container 24 for subsequent removal, performed manually or by a separate system not part of this invention. Such send-out-bags may then be transported to a remote location (not shown) for further processing or storage.

The secondary test tubes, after having been properly labeled with a bar code label and capped, are positioned within sortation trays 21 where they can be manually retrieved for laboratory analysis.

Thus, the automated blood sample processing system herein illustrated, described and defined in the attached claims, provides a fully automated arrangement wherein primary test tubes, each having a quantity of a patient's blood are each positioned into primary tube load areas 1 or 1A and, after automated processing, a laboratory technician can manually remove from the system aliquoted bar code labeled secondary test tubes, in the number required, for laboratory analysis. The system requires a minimal amount of manual labor, is highly compact, and significantly reduces opportunities for contamination from conventional manual processing methods.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. An automated blood sample processing system comprising:

a primary test tube loading means in which primary test tubes having blood samples therein are loaded, a conveyor system for moving test tubes, including primary and secondary test tubes, in selectable routes, said primary test tube loading means being connected to the conveyor system;

a centrifuge;

means for moving said primary test tubes from said conveyor system into said centrifuge wherein said primary test tubes are spun to separate serum from other blood components to provide spun samples and for moving primary test tubes after having been spun from said centrifuge back to said conveyor system;

a secondary test tube loading area in which empty secondary test tubes are loaded, said conveyor system being connected to the secondary test tube loading area;

a pipetting system into which primary test tubes and empty secondary test tubes are moved by said conveyor system;

means in said pipetting system to aliquot spun samples from each of said primary test tubes into a selected number of secondary test tubes;

a bar code printer having means for printing and attaching a bar code label to each of said secondary test tubes;

a capper system into which said secondary test tubes are moved by said conveyor system and in which caps are applied to said secondary test tubes; and a sortation system into which said secondary test tubes are moved by said conveyor system and in which the secondary test tubes are sorted into separate slots in a sortation tray, the secondary test tubes being available for removal from the sortation tray slots for subsequent processing.

2. An automated blood sample processing system according to claim 1 wherein said primary test tubes each have a bar code tag thereon providing at least a patient's number and wherein the system includes means adjacent said conveyor for obtaining information from said bar codes.

3. An automated blood sample processing system according to claim 2 including a system computer having means for input of said information, an output of said system computer being connected to said pipetting system providing instructions that specify a number of secondary samples to be aliquoted from each primary test tube.

4. An automated blood sample processing system according to claim 1 wherein said conveyor system has a first primary tube loading area wherein primary test tubes are placed having primary blood samples therein that have not been centrifuged and that are moved to said centrifuge and a second primary tube loading area wherein test tubes are placed having primary blood samples therein that have been centrifuged, said conveyor moving test tubes from said second test tube loading area in a route that bypasses said centrifuge.

5. An automated blood sample processing system according to claim 3 including a remotely located host computer with which said system computer communicates, the host computer providing patient information to determine the number of aliquots needed from said pipetting system and instructions to said bar code printer by which labels are printed for said secondary test tubes.

6. An automated blood sample processing system according to claim 2 including a reject tray with which said conveyor system connects and means for moving a test tube to said reject tray if the information contained on said bar code label is inconsistent with patient information processed by said system computer.

7. An automated blood sample processing system according to claim 1 including an accumulation area connected with said conveyor system in which test tubes are held in queue as necessary before entering said centrifuge.

8. An automated blood sample processing system according to claim 1 wherein said means for moving test tubes from said conveyor into said centrifuge and for moving test tubes from said centrifuge back to said conveyor includes robotic arm means.

9. An automated blood sample processing system according to claim 4 wherein said conveyor includes a means to merge said test tubes that are centrifuged in said centrifuge with said test tubes that bypass said centrifuge prior to passing all of said test tubes to said pipetting system.

10. An automated blood sample processing system according to claim 1 wherein said pipetting system includes a multi-tip pipetting arm that dispenses appropriate amounts of serum into secondary test tubes.

11. An automated blood sample processing system according to claim 1 including an accumulation area connected with said conveyor system in which test tubes are held in queue as necessary before entering said pipetting system.

12. An automated blood sample processing system according to claim 1 including:
a test tube rack in which primary test tubes are stored after passing said pipetting system.

13. An automated blood sample processing system according to claim 1 including:
a wash system into which said pipetting system moves after said pipetting system has aliquoted spun samples from a primary test tube into a selected number of secondary test tubes wherein said pipetting system is thoroughly washed before being moved to aliquot spun samples from a different primary test tube.

14. An automated blood sample processing system according to claim 3 including:
a printer having means, upon command from said system computer to print out requisitions containing patient demographic or requisition information for use in dispatching batches of capped and labeled secondary test tubes.

* * * * *